Figure 1:
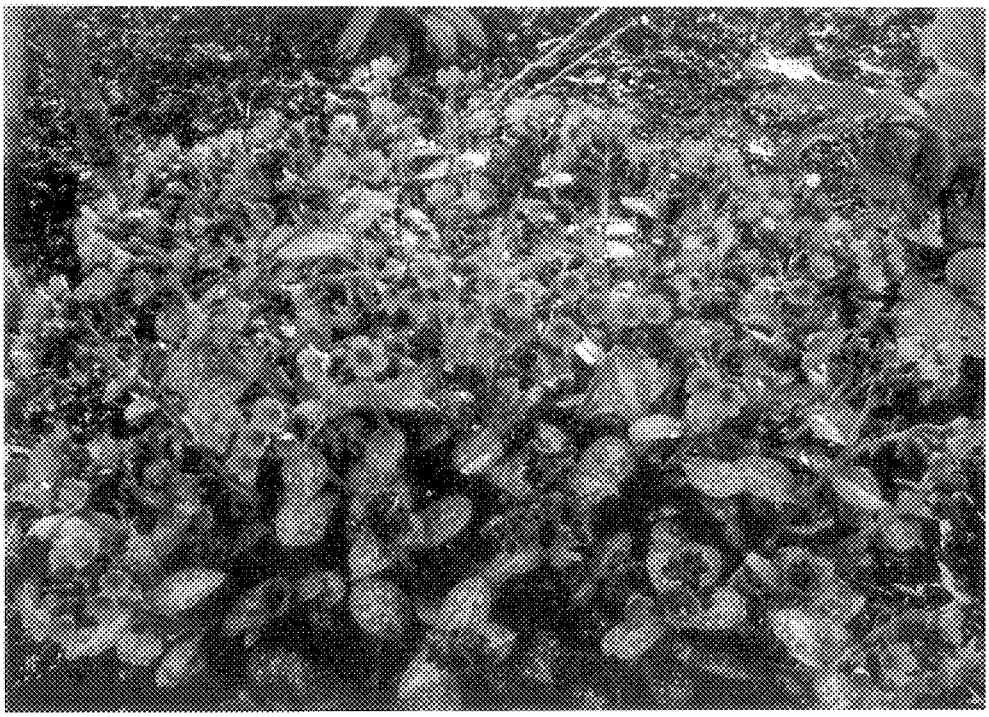

US00PP11234P

United States Patent [19]

Heims

[11] Patent Number: Plant 11,234

[45] Date of Patent: Feb. 22, 2000

[54] PULMONARIA PLANT NAMED 'VICTORIAN BROOCH'

[75] Inventor: Dan M. Heims, Portland, Oreg.

[73] Assignee: Terra Nova Nurseries, Inc., Tigard, Oreg.

[21] Appl. No.: 09/013,677

[22] Filed: Jan. 26, 1998

[51] Int. Cl.[7] ..... A01H 5/00

[52] U.S. Cl. ..... Plt./263

[58] Field of Search ..... Plt./263

[56] References Cited

U.S. PATENT DOCUMENTS

P.P. 8,958 10/1994 Heims ..... Plt./263
P.P. 10,597 9/1998 Heims ..... Plt./263

*Primary Examiner*—Howard J. Locker
*Assistant Examiner*—Kent L. Bell
*Attorney, Agent, or Firm*—Klarquist Sparkman Campbell Leigh & Whinston LLP

[57] ABSTRACT

A new and distinct hybrid of Pulmonaria characterized by very large flowers on a compact scape; distinctive flower color and arrangement; and extended bloom.

1 Drawing Sheet

The present invention relates to a new and distinct hybrid of Pulmonaria which originated as a cross-pollination of pulmonaria 'Margery Fish' (pod parent) (unpatented) (Pulmonaria 'Margery Fish' has been found to be of hybrid origin and cannot be assigned to a specific species) and Pulmonaria 'Leopard' (pollen parent) (unpatented) in the Boraginaceae (Borage family). This new Pulmonaria is a result of a controlled cross of the aforementioned plants at Terra Nova Nurseries, Inc., in Canby, Oreg. Both parents are of hybrid origin and are not patented or protected in any way.

This hybrid was selected as a single plant from a large number of seedlings. The new variety has been reproduced only by asexual propagation (division and tissue culture). Each of the progeny exhibits identical characteristics to the original plant and is unlike any Pulmonaria offered by any American nursery or book (known to the invention) as evidenced by the following characteristics:

(1) Very large flowers on a compact scape; distinctive flower color and arrangement; extended bloomtime of 2.5 months in Canby, Oreg.

(2) Distinctive spotted foliage and excellent mounding form.

(3) Dark ruby calyces and intensified silvering along floral bracts.

Asexual propagation by division and tissue culture done in Tigard, Oreg. shows that the foregoing characteristics and distinctions come true to form and are established and transmitted through succeeding propagations.

BRIEF DESCRIPTION OF THE PHOTOGRAPH

FIG. 1 is a photograph of the plant in full bloom in early March.

DETAILED PLANT DESCRIPTION

The following is a detailed description of the new Pulmonaria hybrid based on observations of specimens in Canby, Oreg. The color descriptions are all based on *The Royal Horticultural Society Colour Chart.*

Ultimate height and width: 25 cm. (8 in.) height by 30 cm. (12 in.) width for one-year's growth from a 1.25-in. plug.

Foliage:

*Type.*—Simple; evergreen in USDA Hardiness Zones 6 to 9, herbaceous in USDA Hardiness Zones 4 and 5.

*Shape.*—Ovate to linear-lanceolate.

*Length.*—25 cm. (12 in.).

*Width.*—8 cm (3 in.).

*Petiole length.*—8 cm. (3 in.).

*Margins.*—Ciliate, entire, slightly undulate.

*Apex.*—Apiculate.

*Base.*—Acute.

*Texture.*—Uniform bristle-like pubescence on both upper and lower surfaces.

*Leaf arrangement.*—Basal clump.

*Venation.*—Reticulate-pinnate.

Flower:

*Flower type.*—Complete, calyx tube urn-shaped; corolla is funnel-shaped, stamens 5, included. Corolla widely flared. Placentation is one-chambered, basal. Fruit is 4 smooth nutlets.

*Flowers.*—R.H.S. 66 A–D–67 A–D Red-Purple Group.

*Flower details.*—Diameter: 1.25–1.5 cm. (⅖–½ in.). Length: 2.1 cm. (⅞ in.). Petal Length: 0.6 cm. (¼ in.) Petal width: 0.8 cm. (⅓ in.). Petal Texture: Smooth, undulate. Base is fused. Petal color is R.H.S. 66 A–D–67 A–D Red-Purple Group with a band of R.H.S. 53A Red Group up the corolla 1.2 cm. (⅜ in.) from the base. Throat Color: R.H.S. 53C Red Group. Calyx Color: R.H.S. 53A Red Group. Clayx Length: 1.2 cm (⅜ in.). Calyx Width: 0.4 cm. (3⁄32 in.). Calyx Texture: Calyx has a uniform, bristle-like pubescence. Peduncles: 8 to 15 cm. (3 to 6 in.). Blooming habit. — Bracted, terminal forked cymes; 12–15 flowers per cyme. Lastingness of individual bloom: 5–7 days. Bloom period. — Third week of February to first week in May in Canby, Oreg.

Color characteristics:

*Foliage.*—Mature leaves, upper surface. — R.H.S. Green Group 137A. Lower surface — R.H.S. Green Group 138B. Petiole base. — R.H.S. Greyed Purple Group 183D (Moderate Red ARS). Upper surface spotting. — R.H.S. Greyed Green Group 196C.

DESCRIPTION OF PARENT PLANTS

This Pulmonaria hybrid has characteristics which makes it unique from its parents: Pulmonaria 'Margery fish' and Pulmonaria 'Leopard'. Pulmonaria 'Margery Fish' is described in the article, "Pulmonaria" by Anthony Husley, June 1987, *HORTICULTURE,* as having large marbled silver and green leaves. The flower color and calyx colors also differ from 'Victorian Brooch'. Pulmonaria 'Leopard' is described in "Pulmonaria" by Anthony Husley, June 1987, *HORTICULTURE,* as having brightly spotted leaves and smaller flowers than most varieties. Pulmonaria 'Leopard' has smaller leaves, lighter calyces, and differs from the unique, brighter flower color of Pulmonaria 'Victorian Brooch'. No other Pulmonaria known to the inventor in commerce resembles Pulmonaria 'Victorian Brooch'.

I claim:

1. A new and distinct hybrid of Pulmonaria plant substantially as shown and described, characterized by its unique flower and form.

* * * * *